United States Patent [19]

Miyahara et al.

[11] Patent Number: 5,151,359
[45] Date of Patent: Sep. 29, 1992

[54] METHOD FOR PRODUCING OF HUMAN TISSUE TYPE PLASMINOGEN ACTIVATOR

[75] Inventors: Shyoichiro Miyahara; Maki Suzuki, both of Yokohama; Atsunori Shindo, Kamakura; Nobumi Kusuhara, Yokohama; Nobuyoshi Makiguchi, Fujisawa, all of Japan

[73] Assignee: Mitsui Toatsu Chemicals Incorporated, Tokyo, Japan

[21] Appl. No.: 347,649

[22] Filed: May 5, 1989

[30] Foreign Application Priority Data

May 19, 1988 [JP] Japan ................................. 63-122644
Dec. 16, 1988 [JP] Japan ................................. 63-316118

[51] Int. Cl.$^5$ .......................... C12N 9/64; C12N 9/48; C12N 9/72; C12N 9/68
[52] U.S. Cl. ................................. 435/226; 435/217; 435/212; 435/215
[58] Field of Search ................ 435/217, 212, 215, 226

[56] References Cited

U.S. PATENT DOCUMENTS

| | | | |
|---|---|---|---|
| 3,732,146 | 5/1973 | Heimburger | 435/217 |
| 4,552,760 | 11/1985 | Marakami et al. | 435/212 |
| 4,554,251 | 11/1985 | Hink, Jr. | 435/240.23 |
| 4,600,580 | 7/1986 | Smith | 435/217 |
| 4,661,453 | 4/1987 | Pollard | 435/212 |
| 4,661,469 | 4/1987 | Sarnoff | 514/2 |
| 4,724,206 | 2/1988 | Rupp et al. | 435/240.22 |
| 4,960,702 | 10/1990 | Rice et al. | 435/226 |

FOREIGN PATENT DOCUMENTS

| | | |
|---|---|---|
| 0133070 | 2/1985 | European Pat. Off. . |
| 0163751 | 11/1985 | European Pat. Off. . |
| 2208486 | 1/1987 | European Pat. Off. . |

OTHER PUBLICATIONS

Kruithof et al, Human Tissue-Type Plasunioger, J. Biochem, 226, 631-636, 1985.
Kaufman et al, Coamplification and Coexpress..., Mol. & Cell. Biol., 5, 7, 1750-1759, 1985.
Markwardt et al, Biological Abstracts, vol. 70, No. 5, abstract 32311, 1980.

Primary Examiner—David M. Naff
Assistant Examiner—Mike Meller
Attorney, Agent, or Firm—Nixon & Vanderhye

[57] ABSTRACT

A method for the production of human tissue type plasminogen activator (tPa) using cells is disclosed. The method includes a supplementation of a p-aminomethyl benzoic acid derivative to a cell culture medium or a tPA producing medium and further an increase of osmotic pressure in the medium to 350 milliosmoles or more/liter. The invention provides a method for producing single-chain tPA in a high concentration and with a relatively small amount of double-chain tPA in the medium.

6 Claims, No Drawings

METHOD FOR PRODUCING OF HUMAN TISSUE TYPE PLASMINOGEN ACTIVATOR

BACKGROUND OF THE INVENTION

1. Field of the Invention

This invention relates to a method for producing tissue type plasminogen activator (hereinafter referred to as tPA) produced by human normal cells.

tPA which is produced and excreted by vascular endothelial cells and various tissue cells lyses fibrin clots, namely thrombi. Thus, tPA is effective as a thrombolytic agent.

2. Description of the Prior Art tPA has two molecular forms, single-chain tPA and double-chain tPA. Thrombolytic activity of double-chain tPA is higher than that of single-chain tPA. So-called tPA has been conventionally developed as the sole double-chain form or the mixture form of the double-chain and the single-chain form.

Double-chain tPA has high fibrinolytic activity, and it is highly possible that double-chain tPA activates plasminogen not in thrombi where fibrinolytic effect is expected but in the blood stream, which often causes clinical bleeding (Japenese Patent Laid-open Pub. No. 118717/1984).

On the other hand, single-chain tPA which is considered to be a precursor of double-chain tPA has high affinity to fibrin and is quickly converted to double-chain tPA once bound to fibrin.

Accordingly, single-chain tPA maximally exhibits plasminogen activity at clotting sites.

Thus, thrombolytic activity of single-chain tPA is relatively low and not exhibited in the blood stream. In consequence, for clinical use, single-chain tPA is in greater demand than double-chain tPA, and an effective method for the production of single-chain tPA is highly requested.

However, in production of single-chain tPA using cells, there is a problem that proteolytic enzymes contained in a medium or produced by the cells (mostly considered to be plasmin or trypsin) convert single-chain tPA to double-chain tPA during production processes, which interferes with effective production of single-chain tPA.

Relevant methods known to solve such problem are described below.

They are a method in which cultivation and subsequent steps are carried out in the presence of aprotinin (European Patent Publication No. 41766), a method in which trypsin inhibitor induced by soybeans or aprotinin is added in the culture medium for tPA-producing cells (Japanese Patent Laid-open Pub. No. 118717/1984), a method in which cultivation or induction production is carried out in a medium supplemented with aprotinin or benzamidine (Japanese Patent Laid-Open Pub. No. 19486/1986) and a method in which sole single-chain tPA is produced by adding aprotinin or 6-aminocapronic acid in a purification process (Biochem. Biophys. Acta 719(2), 318–328, 1982).

Furthermore, particularly in the case where adhesive cells are used, there is a difficult problem that the cells are detached from the wall of a container or the surface of beads during cultivation. To solve this problem, removal of plasmin from the serum and addition of aprotinin are suggested (Kaufman Molecular and Cellular Biology, 5, pp1750).

However, there are many difficulties in practicing these conventional methods on industrial scale. For example, aprotinin to be used is quite expensive. And removal of plasmin from the serum requires complicated processes.

SUMMARY OF THE INVENTION

In the course of intensive study to solve problems of the abovementioned known methods for the production of tPA, the present inventors have found that in tPA production by cells, particularly by adhesive cells, it is effective to add p-aminomethyl benzoic acid derivatives to the medium in order to promote productivity of single-chain tPA and to prevent peeling-off of the cells from the wall of the container or the surface of beads.

Furthermore, the present inventors found that productivity of single-chain tPA can be much improved by increasing the osmotic pressure of the medium supplemented with p-aminomethyl benzoic acid derivatives up to 350 milliosmoles or more/liter by using bicarbonate ion, and thus completed the present invention.

tPA production according to the present invention can be carried out either in parallel with the cell growth or in tPA production process independently of the cell growth.

Namely, the present invention relates to a method of producing human tissue type plasminogen activator, which is characterized in that a p-aminomethyl benzoic acid derivative is added to a cell culture medium and that a p-aminomethyl benzoic acid derivative is added to a tPA producing medium supplemented with a human tissue type plasminogen activator inducer after cultivation of the cells so as to increase productivity of single-chain tPA. Furthermore, the present invention relates to a method of producing human tissue type plasminogen activator, which is characterized in that osmotic pressure of the abovementioned cell culture medium or tPA producing medium, both supplemented with a p-aminomethyl benzoic acid derivative is increased up to 350 milliosmoles or more/liter by using bicarbonate ion so as to greatly improve productivity of single-chain tPA.

According to the present invention, by adding inexpensive p-aminomethyl benzoic acid derivatives in place of expensive aprotinin, which is conventionally used, to the cell culture medium or tPA producing medium, productivity of single-chain tPA can be improved and the peeling-off of the cells from the walls of a container or the surface of beads can be prevented. Furthermore, due to the synergistic effect of bicarbonate ion and a p-aminomethyl benzoic acid derivative added to the medium, productivity of single-chain tPA can be highly improved.

DETAILED DESCRIPTION AND THE PREFERRED EMBODIMENTS

Examples of p-aminomethyl benzoic acid derivatives to be used in the present invention include p-aminomethyl benzoic acid, 3-methoxy-4-aminomethyl benzoic acid, 3-ethoxy-4-aminomethyl benzoic acid, 3-hydroxy-4-aminomethyl benzoic acid, 3-fluoro-4-aminomethyl benzoic acid, 3-chloro-4-aminomethyl benzoic acid, 3-methyl-4-aminomethyl benzoic acid and 2-amino-4-aminomethyl benzoic acid. These p-aminomethyl benzoic acid derivatives are used also in the forms of ester compounds, metal compounds, e.g. alkali metal salts, or the salts thereof, e.g. chlorides.

An example of the tPA producing strain to be used in the present invention is hT-382 cell line (Japanese Patent Laid-Open Pub. No. 126978/1987) which is obtained by transforming mouse C-127 cells with the plasmid constructed with insertions of a part of the BPV-derived plasmid comprising a DNA sequence in which a DNA sequence coding for human tissue type plasminogen activator derived from normal human cells is bound to a human-derived metallothionein promoter, of a part of pBR322 plasmid and of a DNA sequence necessary to stop transcription.

Another example of the tPA producing strain is SV-21-M2.5 K7 cell line (Japanese Patent Laid-Open Pub. No. 126978/1987) which is obtained by transforming CHO (Chinese hamster ovary) cells with the plasmid comprising a DNA sequence in which a DNA sequence coding for human tissue type plasminogen activator derived from normal human cells is bound to SV-40 early promoter and a DNA sequence coding for dihydrofolate reductase, and further by selecting cells carrying amplified genes on a medium supplemented with methotrexate.

Naturally, any kinds of tPA producing cells, for example, those produced in combination with other means such as mutation or adaptation, or those transformed by viruses can be also used.

An example of the cell culture medium in the present invention is a basal medium supplemented with fetal calf serum in an appropriate amount (0 to 10%), and further substances necessary for the cell growth, such as surfactants, amino acids, sugars and salts, if desired.

Furthermore, the tPA producing medium in the present invention is, for example, a basal medium supplemented with fetal calf serum in an appropriate amount (0 to 10%) and with tPA inducing substances such as zinc, cadmium and salts thereof at a concentration of 1 to 10 $\mu$M.

The basal medium in the present invention is a medium comprising, for example, amino acids, vitamins and inorganic salts. Examples of the basal medium include Dulbecco's Modified Eagle Medium (DMEM) (Nissui Pharmaceuticals Co., Ltd.), 199 medium (Nissui Pharmaceuticals Co., Ltd.) and Eagle's Minimal Essential Medium.

According to the present invention, the p-aminomethyl benzoic acid derivatives are added at concentrations ranging from $10^{-4}$ to $10^{-1}$M, more preferably from $10^{-3}$ to $10^{-2}$M, and either to a tPA producing medium or alternatively to a cell culture medium in the case where a tPA producing medium is not used.

Thus, simply by adding p-aminomethyl benzoic acid derivatives to the medium, peeling-off of the cells from the wall of a container or the surface of beads during cultivation can be prevented, and the productivity of single-chain tPA can be improved, without any complicated procedure.

Furthermore, according to the present invention, by increasing the osmotic pressure of the abovementioned cell culture medium or the tPA producing medium, both supplemented with p-aminomethyl benzoic derivatives, up to 350 milliosmoles or more/liter using bicarbonate ion, peeling-off of the cells is prevented, and much improvement in productivity of single-chain tPA can be achieved.

Bicarbonate ion used in the present invention to increase osmotic pressure can be provided as salts, e.g. sodium bicarbonate ($NaHCO_3$), or as carbon dioxide gas.

According to the present invention, bicarbonate ion is used generally in such an amount to make the sum of the osmotic pressure attributed to the supplemented inorganic salts, amino acids, vitamins and the like and that attributed to the bicarbonate ion, 350 milliosmoles or more/liter.

For example, when the osmotic pressure attributed to inorganic salts, amino acids or vitamins is 280 milliosmoles/liter, bicarbonate ion to provide further 70 milliosmoles or more/liter of osmotic pressure is added so as to total 350 milliosmoles or more/liter.

In order to control the osmotic pressure of the medium as abovementioned, for example, sodium bicarbonate ($NaHCO_3$) at a concentration of more than about 3 g/liter, preferably at 3 to 10 g/liter is generally added to the medium.

Means of addition and forms of bicarbonate ion are selected depending on cultivation methods used. For example, when a T-flask, a roller bottle or the like is used, sodium bicarbonate is preferably added to the medium to make the osmotic pressure of the medium 350 to 500 milliosmoles/liter.

Cultivation of cells and production of tPA are preferably carried out in a carbon dioxide gas incubator in either closed or open systems. Further, the amount of carbon dioxide gas dissolved in the medium under the 5% carbon dioxide gas atmosphere is at most about 0.001M which corresponds to about 1 milliosmole/liter. Thus, the overall influence of the atmospheric carbon dioxide gas is negligible in the medium at pH 6.5 to 7.5, the pH ranges used in practice for cultivation.

Furthermore, when cultivation can be carried out in a spinner or a jar, bicarbonate ion is provided by supplying sodium bicarbonate in the medium prior to cultivation and at the same time by blowing carbon dioxide gas in the system, so as to maintain the total osmotic pressure in the system at 350 to 500 milliosmoles/liter.

Further, p-aminomethyl benzoic acid derivatives may be added to the basal medium during preparation or after making the medium hypertonic by bicarbonate ion.

For cell cultivation, any known methods are applicable. For example, the following method can be used.

Namely, an appropriate amount of cells are inoculated in a medium supplemented with a tPA inducer, if desired, in a Roux flask and then incubated at an appropriate temperature for an appropriate time in a carbon dioxide gas incubator for tPA production in parallel with cell growth.

Alternatively, cells are inoculated in a medium in a Roux flask and then allowed to grow at an appropriate temperature for an appropriate time in a carbon dioxide gas incubator. When the cells are grown to confluent, the medium is replaced by a tPA producing medium and then incubation is continued in the carbon dioxide gas incubator at an appropriate temperature for an appropriate time for tPA production.

For example, when a 75-cm$^2$ Roux flask is used, cells are inoculated at the concentration of 0.5 to $2.0 \times 10^5$/ml and incubated at 37° C. for 3 to 4 days for the growth in parallel with tPA production.

Alternately, for example, when a 75-cm$^2$ Roux flask is used, cells are inoculated at the concentration of 1 to $2 \times 10^5$/ml and incubated at 37° C. for 3 to 4 days for the cell growth. Then, the medium is replaced by a tPA producing medium and the incubation is continued at 37° for 1 to 3 days for tPA production.

EXAMPLES

The present invention will be described more specifically by the following Examples:

EXAMPLE 1

The cells used for the tPA production were those of the abovementioned hT-382 strain.

In 75-cm² Roux flasks, 20 ml each of Dulbecco's Modified Eagle Medium (DMEM) supplemented with 10% fetal calf serum which had been heat-inactivated and 10 μM zinc chloride was placed. To each medium, aprotinin, p-aminomethyl benzoic acid or 3-methoxy-4-aminomethyl benzoic acid is added in the specified amount shown in Table 1. Each culture medium thus prepared was inoculated with the abovementioned cells at a concentration of $1.0 \times 10^5$ cells/ml.

The cells were incubated at 37° C. for 4 days. When the cells were grown to confluent (about $10 \times 10^5$ cells/ml), concentrations of single-chain tPA and double-chain tPA in the culture were determined by the analysis described below. Results are shown in Table 1.

The method for the analysis of single-chain tPA and double-chain tPA in the culture is as follows.

I ELISA Method (1) Monoclonal antibodies to single-chain tPA (PAM-1, American Diagonotica Co.) and monoclonal antibodies to single-chain tPA plus double-chain tPA (PAM-2, American Diagonotica Co.) are diluted with a coating solution to 10 micrograms/ml, and 50 microliters each of the diluted solutions is dispensed into the wells of an ELISA plate (96 wells, Corning Glass Works). The plate is allowed to stand for 2 hours at room temperature, and then the fluid in the wells is discarded.

(2) Each of the wells is washed with a washing solution, and then filled with a blocking solution. The plate is allowed to stand for 30 minutes at room temperature. Fifty microliters each of 1000-~2000-fold diluted sample solutions and standard solutions (0, 1, 2, 4 and 8 ng/ml) is added into each of the wells, and the plate is allowed to stand for 2 hours.

(3) Each of the wells is again washed with the washing solution, and then an anti-tPA rabbit antibody is added into each well.

(4) Each of the wells is again washed with the washing solution, and then 50 microliters of a 500-fold diluted solution of goat anti-rabbit IgG and alkaline phosphatase conjugate (Sigma) is added into each well. The plate is allowed to stand for 1 hour.

(5) Each of the wells is again washed with the washing solution, and then 50 microliters of a substrate solution (p-nitrophenyl phosphate, 0.6 mg-ml, Sigma) is added into each well. The plate is allowed to stand for 30 minutes.

(6) Fifty microliters of a 3N NaOH solution is added to each of the wells to stop enzymatic reaction.

(7) Absorption at 405 nm is read with a commercially available ELISA reader.

(8) A measuring line is drawn using the readings of standards, and the tPA concentrations in the samples are determined.

(9) Calculations are made as follows.

Single-chain tPA content (mg/liter)=Measurement for PAM-1

Double-chain tPA content (mg/liter)=Measurement for PAM-2-measurement for PAM-1

II. Qualitative Analysis by Immunoblotting (1) Each of the culture solutions is treated in a sample solution for electrophoresis with or without beta-mercaptoethanol which reduces proteins in the sample. The electrophoresis is carried out according to the method of Laemmli (1970).

(2) After the electrophoresis, proteins are electritically transferred onto a nitrocellulose filter by the method of Towbin et al. (1979).

(3) Non-specific protein absorbing sites are saturated with bovine serum albumin.

(4) The nitrocellulose filter is treated with primary antibodies, i.e. anti-tPA antibodies (for example, goat-derived or rabbit-derived polyclonal antibodies or mouse-derived monoclonal antibodies), to allow to react with tPA on the nitrocellulose filter.

(5) Secondary antibodies are allowed to react with anti-tPA antibodies and then allowed to react with alkali-phosphatase-bound antibodies against the secondary antibodies.

(6) Color reaction is carried out using bromo-chloroindolyl phosphate, as a substrate for alkali phosphatase, which is dissolved in a solution containing nitrobluetetrazorium, so as to detect tPA or decomposed fractions or aggregates thereof on the nitrocellulose filter.

In the blotting with single-chain tPA, a major band at about 70 kd is obtained in both reduced and non-reduced samples. In the blotting with double-chain tPA, the major band at about 70 kd similar to that with single-chain tPA is obtained in the non-reduced sample while in reduced samples, bands at about 30 kd and about 40 kd are obtained and the band at about 70 kd is not. The bands found at about 70 kd, about 30 kd and about 40 kd in the immunoblotting of these reduced and non-reduced samples are compared so as to qualitatively estimate the rate of single-chain tPA to double-chain tPA in the samples.

Although the immunoblotting analysis is a qualitative measurement, it was used to confirm the quantative data conventionally obtained by ELISA.

As evidently shown in Table 1, in the culture supplemented with p-aminomethyl benzoic acid or its derivative, peeling-off of the cells was relatively insignificant and single-chain tPA production was improved.

Particularly, with p-aminomethyl benzoic acid or its derivative at the concentration of $10^{-4}$M or more, effect was comparable to or exceeding that with aprotinin.

TABLE 1

| | Conc. | Amount of (mg/l) sc-tPA* | Amount of (mg/l) dc-tPA** | Rate of sc-tPA (%) | Peeling-off*** |
|---|---|---|---|---|---|
| Control | — | 1.8 | — | 52 | +++ |
| Aprotinine (KIU/ml) | 80 | 6.2 | 0.5 | 92 | + |
| | 40 | 6.4 | 0.4 | 94 | + |
| | 20 | 5.3 | 0.6 | 90 | + |
| p-Aminomethyl benzoic acid (M) | $10^{-2}$ | 7.2 | 0.3 | 96 | — |
| | $10^{-4}$ | 6.8 | 0.6 | 92 | — |
| | $10^{-6}$ | 4.9 | 1.1 | 82 | + |
| 3-Methoxy-4-aminomethyl benzoic acid (M) | $10^{-2}$ | 6.8 | 0.5 | 93 | — |
| | $10^{-4}$ | 6.4 | 0.6 | 92 | — |
| | $10^{-6}$ | 4.7 | 1.0 | 82 | + |

*Single-chain tPA.
**Double-chain tPA.
***Observed with naked eyes.
− < + < ++ < +++ In order of ascending degree of peeling-off.

EXAMPLE 2

The cell line used in Example 1 was similarly used. The cells were inoculated at a concentration of $1.0 \times 10^5$ cells/ml in 20 ml each of Dulbecco's Modified Eagle Medium (DMEM) supplemented with 10% heat-inactivated fetal calf serum in 75-cm² Roux flasks.

The cells were incubated at 37° C. for 4 days. When the cells were grown to confluent (about $10 \times 10^5$ cells/ml), the medium was discarded and then replaced with 20 ml of the tPA producing medium having the same composition as described above except that zinc chloride at a concentration of 10 μM and respective additives shown in Table 2 were supplemented. Incubation was continued in carbon dioxide gas incubator at 37° C. for 2 days. The concentrations of single-chain tPA and double-chain tPA in the culture were determined as described in Example 1. Results are shown in Table 2.

As evidently shown in Table 2, in the culture supplemented with p-aminomethyl benzoic acid or its derivative, peeling-off of the cells was relatively insignificant and single-chain tPA production was improved. Particularly, with p-aminomethyl benzoic acid or its derivative at a concentration of $10^{-4}$M or more, effect exceeded that with aprotinin.

TABLE 2

| | Conc. | Amount of (mg/l) sc-tPA* | Amount of (mg/l) dc-tPA** | Rate of sc-tPA (%) | Peeling-off*** |
|---|---|---|---|---|---|
| Control | — | 3.0 | 4.2 | 42 | +++ |
| Aprotinin (KIU/ml) | 80 | 8.8 | 1.0 | 90 | + |
|  | 40 | 8.6 | 0.5 | 94 | + |
|  | 20 | 7.8 | 1.4 | 85 | ++ |
| p-Aminomethyl benzoic acid (M) | $10^{-2}$ | 9.8 | 0 | 100 | − |
|  | $10^{-4}$ | 9.4 | 0.4 | 96 | − |
|  | $10^{-6}$ | 7.8 | 1.2 | 86 | + |
| 3-Methoxy-4-aminomethyl benzoic acid (M) | $10^{-2}$ | 9.2 | 0.4 | 96 | − |
|  | $10^{-4}$ | 8.7 | 1.0 | 90 | + |
|  | $10^{-6}$ | 6.8 | 2.0 | 77 | ++ |

*Single-chain tPA.
**Double-chain tPA.
***Observed with naked eyes.
− < + < ++ < +++ In order of ascending degree of peeling-off.

EXAMPLE 3

The cells used for tPA production were those of SV-21-M2.5 K7 cell line which was obtained by transforming CHO (Chinese hamster ovary) cells with the plasmid comprising a DNA sequence in which a DNA sequence coding for tPA was bound to SV-40 early promoter and a DNA sequence coding for dihydrofolate reductase, and further by selecting the transformed cells carrying amplified genes on a medium supplemented with methotrexate. The tPA production was carried out in the same manner as described in Example 1 except that zinc chloride was not added to the medium. The results are shown in Table 3. As evident in Table 3, peeling-off of the cells was relatively insignificant and single-chain tPA production was improved in all the cases. Particularly, with p-aminomethyl benzoic acid, the effect was remarkable.

TABLE 3

| | Conc. | Amount of (mg/l) sc-tPA* | Amount of (mg/l) dc-tPA** | Rate of sc-tPA (%) | Peeling-off*** |
|---|---|---|---|---|---|
| Control | — | 1.2 | 1.3 | 49 | +++ |

TABLE 3-continued

| | Conc. | Amount of (mg/l) sc-tPA* | Amount of (mg/l) dc-tPA** | Rate of sc-tPA (%) | Peeling-off*** |
|---|---|---|---|---|---|
| Aprotinin (KIU/ml) | 80 | 3.2 | 0.4 | 90 | + |
|  | 40 | 3.4 | 0.3 | 93 | + |
|  | 20 | 2.7 | 0.4 | 86 | ++ |
| p-Aminomethyl benzoic acid (M) | $10^{-2}$ | 3.8 | 0.2 | 94 | − |
|  | $10^{-4}$ | 3.8 | 0.3 | 92 | − |
|  | $10^{-6}$ | 3.6 | 0.7 | 83 | + |
| 3-Methoxy-4-aminomethyl benzoic acid (M) | $10^{-2}$ | 3.5 | 0.4 | 90 | − |
|  | $10^{-4}$ | 3.2 | 0.5 | 87 | + |
|  | $10^{-6}$ | 2.6 | 0.8 | 76 | ++ |

*Single-chain tPA.
**Double-chain tPA.
***Observed with naked eyes.
− < + < ++ < +++ In order of ascending degree of peeling-off.

EXAMPLE 4

The cells used for tPA production were those of hT-382 cell line which was obtained by transforming mouse C-127 cells with the plasmid constructed with insertions of a part of the BPV-derived plasmid comprising a DNA sequence in which a DNA sequence coding for tPA was bound to human-derived metallothionein promoter, of a part of pBR322 plasmid and of a DNA sequence necessary to stop transcription.

Into 75-cm² Roux flasks, 20 ml each of DMEM medium supplemented with 10% heat-inactivated fetal calf serum and 10 uM zinc chloride was poured. To each medium, aprotinin (40 KIU/ml) or p-aminomethyl benzoic acid at a concentration of $10^{-2}$M and furthermore sodium bicarbonate in specified amounts shown in Table 4 were supplemented. Each of the medium thus prepared was inoculated with the abovementioned cells at a concentration of $1.0 \times 10^5$ cells/ml.

The cells were incubated in a 5% carbon dioxide gas incubator at 37° C. for 4 days. When the cells were grown to confluent (about $10 \times 10^5$ cells/ml), concentrations of single-chain tPA in the individual cultures were determined by the method described above. The results are shown in Table 4.

Measurements of osmotic pressure were made using Simazu Osmometer after the sampling for tPA determination.

As evidently shown in Table 4, when the osmotic pressure of the medium exceeded 300 milliosmoles/liter, not only single-chain tPA production rate but also over all tPA production were improved. Furthermore, single-chain tPA production was more greatly improved in the medium supplemented with p-aminomethyl benzoic acid than in the medium supplemented with aprotinin.

TABLE 4

| NaHCO₃ (g/l) | Osmotic pressure (milliosmoles) | Additive | sc-tPA* (mg/l) | sc-tPA rate (%) |
|---|---|---|---|---|
| 1.0 | 300 | AP** | 6.4 | 90 |
|  |  | PAMBA*** | 7.2 | 96 |
| 5.0 | 380 | AP | 10.2 | 92 |
|  |  | PAMBA | 26.3 | 98 |
| 7.5 | 450 | AP | 14.3 | 92 |
|  |  | PAMBA | 28.2 | 97 |
| 10.0 | 520 | AP | 7.4 | 90 |
|  |  | PAMBA | 14.3 | 98 |

*Single-chain tPA
**Aprotinin
***p-Aminomethyl benzoic acid

EXAMPLE 5

The cells for tPA production were those of the same strain as used in Example 4. The cells were inoculated at the concentration of $1.0 \times 10^5$ cells/ml in 20 ml each of DMEM supplemented with 10% heat-inactivated fetal calf serum in 75-cm$^2$ Roux flasks.

The cells were incubated in a 5% carbon dioxide gas incubator at 37° C. for 4 days. When the cells were grown to confluent ($10 \times 10^5$ cells/ml), the medium was discarded and then replaced with 20 ml each of the medium which had the same composition as described above except that zinc chloride (10 μM) and further aprotinin (40 KIU/ml) and p-aminomethyl benzoic acid ($10^{-2}$M) as well as sodium bicarbonate at the concentrations specified in Table 4 were respectively supplemented. The cells were again incubated in a carbon dioxide gas incubator at 37° C. for 2 days for tPA production. The concentrations of tPA in the individual culture were determined as described in Example 1. Results are shown in Table 5.

Similar to Example 4, remarkable improvement in productivity of single-chain tPA was observed in the culture in which p-aminomethyl benzoic acid was supplemented and osmotic pressure was increased.

TABLE 5

| NaHCO$_3$ (g/l) | Osmotic pressure (milliosmoles) | Additive | sc-tPA* (mg/l) | sc-tPA rate (%) |
|---|---|---|---|---|
| 1.0 | 300 | AP** | 8.6 | 90 |
|  |  | PAMBA*** | 9.8 | 100 |
| 5.0 | 380 | AP | 24.3 | 88 |
|  |  | PAMBA | 38.2 | 95 |
| 7.5 | 450 | AP | 32.0 | 92 |
|  |  | PAMBA | 45.0 | 96 |
| 10.0 | 520 | AP | 21.0 | 94 |
|  |  | PAMBA | 32.0 | 95 |

*Single-chain tPA
**Aprotinin
***p-Aminomethyl benzoic acid

EXAMPLE 6

The cells used for the tPA production were those of SV-21-M2.5 K7 cell line that was obtained by transforming CHO (Chinese hamster ovary) cells with the plasmid comprising a DNA sequence in which a DNA sequence coding for tPA was bound to the SV-40 early promoter and a DNA sequence coding for dihydrofolate reductase and then by selecting cells carrying amplified genes on a medium supplemented with methotrexate.

The tPA production was carried out in the same manner as described in Example 4 except that the medium contained no zinc chloride. The results are shown in Table 6.

Remarkable effects were found not only in productivity of single-chain tPA but also in the rate of single-chain tPA.

TABLE 6

| NaHCO$_3$ (g/l) | Osmotic pressure (milliosmoles) | Additive | sc-tPA* (mg/l) | sc-tPA rate (%) |
|---|---|---|---|---|
| 1.0 | 300 | AP** | 3.4 | 93 |
|  |  | PAMBA*** | 3.8 | 94 |
| 5.0 | 380 | AP | 8.2 | 88 |
|  |  | PAMBA | 20.3 | 96 |
| 7.5 | 450 | AP | 10.4 | 92 |
|  |  | PAMBA | 26.5 | 100 |
| 10.0 | 520 | AP | 7.5 | 90 |
|  |  | PAMBA | 22.3 | 92 |

*Single-chain tPA
**Aprotinin
***p-Aminomethyl benzoic acid

EXAMPLE 7

The cells used for the tPA production were those of the same strain as used in Example 4. The cells ($10^8$ cells) were inoculated at the concentration of $1.0 \times 10^5$ cells/ml in 1 liter each of DMEM supplemented with 10% heat-inactivated fetal calf serum in 1-liter spinner flasks (total capacity of about 1.5 liter) each equipped with stirring blades, pH electrodes, DO electrodes and a pipe for blowing gas. Seed cells used had been cultured in advance in the abovementioned medium in a roller bottle. Incubation was carried out at 37° C. for 4 days. When the cell concentration reached $10^6$ cells/ml, the abovementioned medium was discarded and replaced for tPA production with 1 liter each of DMEM supplemented with 5% heat-inactivated fetal calf serum, aprotinin (40 KIU/ml) or p-aminomethyl benzoic acid ($10^{-2}$M) and zinc chloride (10 μM).

In order to maintain the osmotic pressure of the medium as shown in Table 7, 5% carbon dioxide gas was occasionally blown into the bottle. pH was adjusted with NaOH. Further, DO was maintained at 1 PPM and the temperature at 37°. Medium changes were carried out once a day for 5 days, thus tPA fractions were recovered totally five times.

As evidently shown in Table 7, similar effects as shown in Example 4 was observed when the osmotic pressure was controlled by blowing carbon dioxide gas into the medium.

TABLE 7

| Osmotic pressure (milliosmoles) | Additive | Single-chain tPA (mg/ml) | | | | | |
|---|---|---|---|---|---|---|---|
|  |  | 1 | 2 | 3 | 4 | 5 | Total |
| 300 | AP* | 4.3 | 6.2 | 7.7 | 4.8 | 4.0 | 27.0 |
|  |  | (87) | (88) | (91) | (90) | (88) |  |
|  | PAMBA** | 5.2 | 7.4 | 10.0 | 6.2 | 4.6 | 33.4 |
|  |  | (93) | (96) | (97) | (95) | (96) |  |
| 450 | AP | 10.1 | 13.4 | 17.2 | 16.8 | 12.2 | 69.7 |
|  |  | (90) | (89) | (93) | (92) | (91) |  |
|  | PAMBA | 12.4 | 28.0 | 36.2 | 36.4 | 38.2 | 151.2 |
|  |  | (96) | (98) | (98) | (97) | (98) |  |

Rates of single-chain tPA (%) were given in parentheses.
*Aprotinin
**p-Aminomethyl benzoic acid

What is claimed is:

1. A method of producing predominantly single-chain human tissue type plasminogen activator with only minor amounts of double-chain human tissue type plasminogen activator, said method comprising culturing human tissue type plasminogen activator-producing cells in a cell culture medium supplemented with p-aminomethyl benzoic acid or a derivative thereof, so that the p-aminomethyl benzoic acid or its derivative directly inhibits the conversion of single-chain t-PA into double-chain t-PA, whereby t-PA is produced predominantly as single-chain t-PA in parallel with the growth of the cells.

2. A method of producing predominantly single-chain human tissue type plasminogen activator with only minor amounts of double-chain human tissue type plasminogen activator, said method comprising
(a) growing human tissue type plasminogen activator-producing cells in a cell culture medium, and thereafter
(b) incubating the cells in a medium for producing human tissue type plasminogen activator, said medium supplemented with a human tissue type plasminogen activator inducer and p-aminomethyl benzoic acid or a derivative thereof, so that the p-aminomethyl benzoic acid or its derivative directly inhibits the conversion of single-chain t-PA into double-chain t-PA, whereby t-PA is produced predominantly as single-chain tPA.

3. A method as set forth in claim 1, in which bicarbonate ion equivalent to 3-10 g/l of $NaHCO_3$ is supplied to said cell culture medium to increase the osmotic pressure of the medium to a range of 350 to 520 milliosmoles/liter.

4. A method as set forth in claim 2, in which bicarbonate ion equivalent to 3-10 g/l of $NaHCO_3$ is supplied to said medium for producing t-PA to increase to osmotic pressure of the medium to a range of 350 to 520 milliosmoles/liter.

5. A method as set forth in claim 1, 2, 3 or 4 in which said p-aminomethyl benzoic acid derivative is p-aminomethyl benzoic acid.

6. A method as set forth in claim 1, 2, 3 or 4 in which the concentration of said p-aminomethyl benzoic acid derivative in the medium is present in the range of $10^{-4}$ to $10^{-1}$M.

* * * * *